United States Patent
Yi (10) Patent No.: US 12,053,395 B2
(45) Date of Patent: Aug. 6, 2024

(54) ELBOW STRUCTURE FOR ELECTRONIC ARTIFICIAL ARM

(71) Applicant: MAND.RO CO., LTD., Bucheon-si (KR)

(72) Inventor: Sang Ho Yi, Seoul (KR)

(73) Assignee: MAND.RO CO., LTD., Bucheon-si (KR)

( * ) Notice: Subject to any disclaimer, the term of this patent is extended or adjusted under 35 U.S.C. 154(b) by 436 days.

(21) Appl. No.: 17/419,632

(22) PCT Filed: Dec. 31, 2018

(86) PCT No.: PCT/KR2018/016989
§ 371 (c)(1),
(2) Date: Jun. 29, 2021

(87) PCT Pub. No.: WO2020/141618
PCT Pub. Date: Jul. 9, 2020

(65) Prior Publication Data
US 2022/0079780 A1    Mar. 17, 2022

(51) Int. Cl.
*A61F 2/58*       (2006.01)
*A61F 2/70*       (2006.01)
*A61F 2/68*       (2006.01)

(52) U.S. Cl.
CPC ............... *A61F 2/582* (2013.01); *A61F 2/70* (2013.01); *A61F 2002/6836* (2013.01)

(58) Field of Classification Search
CPC .... A61F 2/582; A61F 2/70; A61F 2002/6836; A61F 2/58
See application file for complete search history.

(56) References Cited

U.S. PATENT DOCUMENTS

| | | | |
|---|---|---|---|
| 10,919,161 B2 * | 2/2021 | Smith | F16D 25/14 |
| 11,246,720 B2 * | 2/2022 | Wahl | A61F 2/582 |
| 11,464,654 B2 * | 10/2022 | Lipsey | H02K 7/116 |
| 2005/0188521 A1 | 9/2005 | Simon et al. | |
| 2008/0045374 A1 | 2/2008 | Weinberg et al. | |
| 2023/0248544 A1 * | 8/2023 | Langenfeld | A61F 2/583 623/64 |

FOREIGN PATENT DOCUMENTS

| | | |
|---|---|---|
| CN | 107041825 A | 8/2017 |
| CN | 108451747 A | 8/2018 |
| KR | 10-0649892 B1 | 11/2006 |
| KR | 10-1247705 B1 | 3/2013 |
| KR | 10-1478102 B1 | 1/2015 |

* cited by examiner

*Primary Examiner* — Bruce E Snow
(74) *Attorney, Agent, or Firm* — NKL LAW; Jae Youn Kim (57) ABSTRACT

Disclosed is an elbow structure, for an electronic artificial arm, which hinge-connects the humeral part and radioulnar part and enables the joint movement of the humeral part and radioulnar part about one central axis. The elbow structure for an electronic artificial arm comprises: a first connection unit of which one end is connected to the radioulnar part and which has inside the other end a plurality of driving portions provided concentrically with and a predetermined distance away from the central axis and each having a gear on one end; and a second connection unit of which one end is connected to the humeral part and which has teeth portions aligned in a circle so as to interlock and rotate with the gears of the plurality of driving portions in the outer direction.

5 Claims, 9 Drawing Sheets

ELBOW STRUCTURE FOR ELECTRONIC ARTIFICIAL ARM

TECHNICAL FIELD

This application is a result of development of integrated finger and palm built-in drive system for electroMG prostheses, supported by Korea Medical Device Development Fund (No. KMDF_PR_20200901_0175-01(1711138363)).

The present invention relates to an elbow structure of an electronic prosthetic hand. More particularly, the present invention relates to an elbow structure that prevents an overload while gripping and transporting an object with an electronic prosthetic hand and may more easily lift up the object.

BACKGROUND ART

A user whose one hand or both hands are amputated in an amputation accident uses a prosthetic hand for daily life. In detail, various types of prosthetic hands are provided depending on the position of an affected part and have been developed from a cosmetic prosthetic hand having only the outer shape of a hand without a driving function to a prosthetic hand that lifts up an arm to grip and transport objects by driving a joint part using a predetermined muscular strength. In particular, in the case of an electronic prosthetic hand, performance close to that of an actual hand of a person can be achieved. However, in order to lift up a heavy object as described above like an actual hand, a high-output driving unit should be mounted on an elbow part located between an upper arm and a lower arm of the arm and configured to provide a joint motion. However, since the high-output driving unit for generating power with a motor or the like has a large size, it is difficult to use the high-output driving unit in a state in which the high-output driving unit is accommodated in the elbow part. Further, even when the high-output driving unit is inserted into the elbow part, the elbow part is enlarged, thereby causing the user to feel repulsion for the outer shape. Further, noise generated while the high-output driving unit generates power is a factor that causes stress in a daily life of the user. Further, when a mechanical elbow using a hinge connection method is used while excluding the high-power driving unit, there is a problem in that it is difficult to lift up a heavy object and the mechanical elbow is easily damaged. Additionally, manufacturing costs of the high-power driving unit are expensive, thereby hindering mass production and purchases of users. Thus, there is a need for the development of an electronic prosthetic hand which can easily lift up an object without mounting the high-power driving unit and which the users can easily make decision to purchase.

RELATED ART DOCUMENT

Patent Document

Related Art Document 1: Korean Patent No. 10-1247705 (registered on Mar. 20, 2013)
Related Art Document 2: Korean Patent No. 10-0649892 (registered on Nov. 20, 2006)

DISCLOSURE

Technical Problem

The present invention is directed to providing an elbow of an electronic prosthetic hand capable of easily gripping and transporting a heavy object without using a driving unit having a large size and generating a lot of noise.

The present invention is also directed to providing an elbow of an electronic prosthetic hand capable of preventing an upper arm and a lower arm from being bent at an excessively large angle.

The purpose of the present invention is to prevent an overload from occurring due to the concentration of a load when the lower arm is lifted up in a state in which the upper arm and the lower arm are collinearly arranged.

Technical Solution

One aspect of the present invention provides an elbow structure of an electronic prosthetic hand in which an upper arm and a lower arm are hinge-connected and which jointly moves the upper arm and the lower arm about one central axis, the elbow structure including a first connection part that has one end connected to the lower arm and is provided with a plurality of driving units disposed on a concentric circle spaced a predetermined interval from the one central axis in the other end thereof and having one ends provided with gears, and a second connection part that has one end connected to the upper arm and has a toothed part disposed in a circular shape to be engaged with the gears of the plurality of driving units in an outward direction and rotated therewith.

Advantageous Effects

According to the present invention, in a state in which a second connection part is fixed, a first connection part performs a first rotational movement and a second rotational movement using a driving unit and a gear, and thus an object can be easily griped and transported.

Further, in the present invention, since the plurality of driving units are provided, without using a high-output driving unit, an elbow part of an electronic prosthetic hand can be miniaturized and simplified, noise can be minimized, and thus a user's discomfort can be minimized.

MODES OF THE INVENTION

Hereinafter, embodiments of the present invention will be described in detail with reference to the accompanying drawings so that those skilled in the art to which the present invention pertains may easily implement the present invention. However, the present invention may be implemented in various different forms and is not limited to the embodiments described herein. Further, in order to clearly disclose the present invention in the drawings, parts irrelevant to the present invention will be omitted, and in the drawings, the same or similar reference numerals indicate the same or similar components.

The purpose and effect of the present invention may be naturally understood or made clearer by the following description, and the purpose and effect of the present invention is not limited to only the following description.

The purpose, the feature, and the advantage of the present invention will become more apparent from the following detailed description. Further, in the description of the present invention, when it is determined that the detailed description of widely known related technologies may make the subject matter of the present invention unclear, the detailed description will be omitted.

Hereinafter, the embodiments of the present invention will be described in detail with reference to the accompanying drawings.

Figure 1:
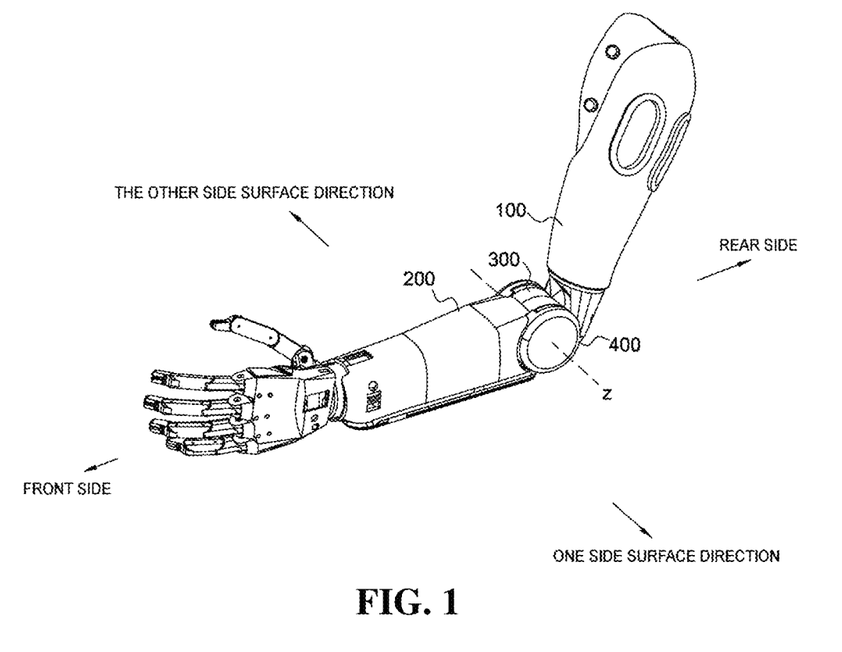
FIG. 1 is a view illustrating an entire elbow for an electronic prosthetic hand according to one embodiment of the present invention.

FIG. 1 is a view illustrating the entire elbow for an electronic prosthetic hand according to one embodiment of the present invention. Prior to describing the present invention in detail, a term "one side surface direction" means a lower right direction in FIG. 1. In detail, the term "one side surface direction" means a leftward direction from a user's point of view when the electronic prosthetic hand illustrated in FIG. 1 and used for a left arm is worn. Further, a term "the other side surface direction" refers to an upper left direction in FIG. 1 and means a rightward direction toward a right arm with respect to the user wearing the electronic prosthetic hand as described above. Further, terms "upward direction" and "downward direction" mean an upward direction and a downward direction in the drawings unless otherwise stated. Further, a term "front side" means a direction in which a lower arm 200 is directed according to the present invention. In detail, the term "front side" means a direction in which one end of the lower arm 200 having a separate finger part formed at the one end thereof is directed, and a term "rear side" means a direction opposite to the "front side." Further, a term "one central axis z" means a central axis of a second connection part 400. In detail, the term "one central axis z" means a central axis of the second connection part 400 hinge-connecting an upper arm 100 and the lower arm 200 and having a circular cross section. Thus, the upper arm 100 and the lower arm 200 may jointly move about the one central axis z. Further, a term "first rotational movement s1" means a state in which the lower arm 200 rotates so that an angle between the upper arm 100 and the lower arm 200 increases, and a term "second rotational movement s2" means a state in which the lower arm 200 rotates to approach the upper arm 100. That is, when the lower arm 200 performs the first rotational movement s1, the upper arm 100 and the lower arm 200 are spread apart, and when the lower arm 200 performs the second rotational movement s2, the upper arm 100 and the lower arm 200 are closed so that the upper arm 100 and the lower arm 200 approach each other.

The electronic prosthetic hand according to the present invention includes the lower arm 200 that grips an object, a first connection part 300 having one end connected to the lower arm 200, a second connection part 400 connected to the first connection part 300, and the upper arm 100 connected to one end of the second connection part 400.

As described above, the lower arm 200 is configured to lift up or transport an object while gripping the object. To this end, the lower arm 200 is formed in the same shape as a real hand of a person. In detail, a separate finger part is formed at one end of the lower arm 200, and the other end of the lower arm 200 is connected to the first connection part 300. Further, the lower arm 200 is formed to have a range from the real hand to an elbow part of a person. Accordingly, as the lower arm 200 is jointly moved by rotational movement of the first connection part 300, an angle between the lower arm 200 and the upper arm 100 varies, and thus the height of the gripped object may be adjusted. In detail, the lower arm 200 performs the first rotational movement s1 by the first connection part 300 and the second connection part 400 to increase the angle between the lower arm 200 and the upper arm 100, and performs the second rotational movement s2 to be lifted up so as to decrease the angle between the lower arm 200 and the upper arm 100.

The upper arm 100 is connected to the second connection part 400 for rotating the lower arm 200 and supports the lower arm 200 from the body of a person. To this end, one end of the upper arm 100 is connected to the body or an affected part of a person, and the other end thereof is connected to one end of the second connection part 400 which will be described above. That is, the upper arm 100 has a range from the affected part to the elbow of a person. Thus, in a state of being fixed in a downward direction of the upper arm 100, the second connection part 400 may allow the lower arm 200 to perform the first rotational movement s1 and the second rotational movement s2 by being fastened to the first connection part 300 and being rotated.

Figure 2:
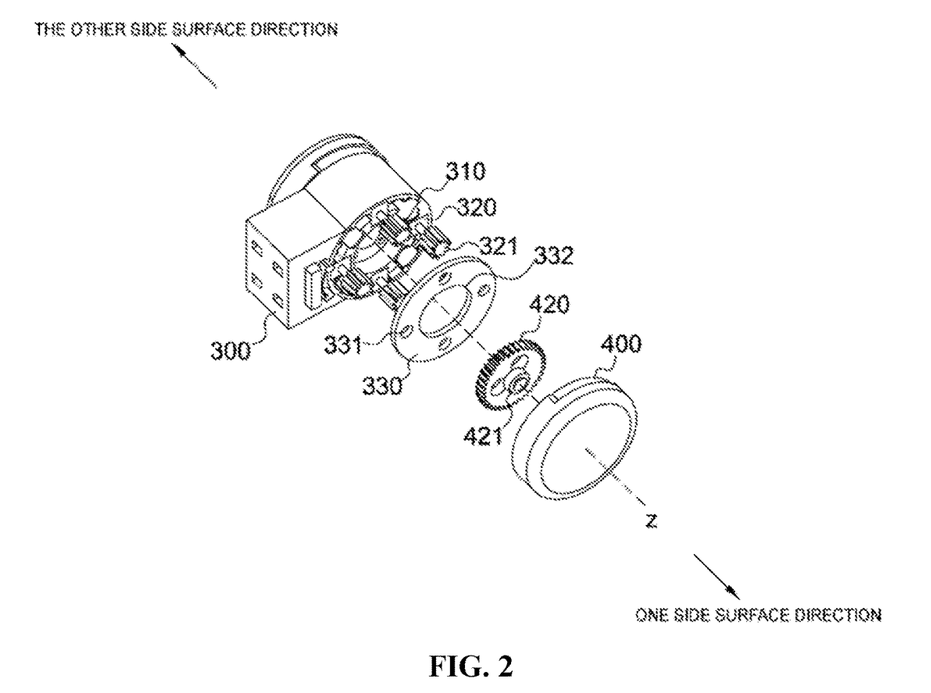
FIG. 2 is a view illustrating a first connection part and a second connection part according to one embodiment of the present invention.
Figure 3:
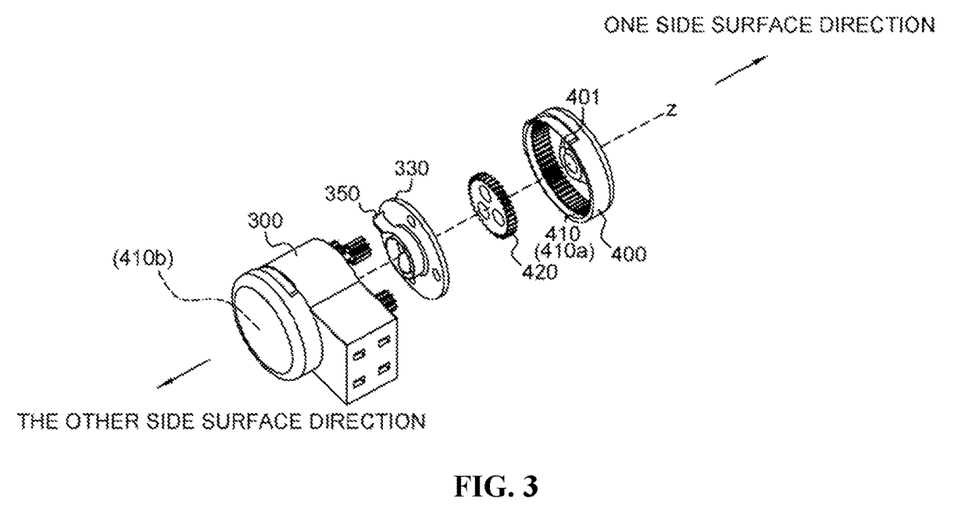
FIG. 3 is a view illustrating the first connection part and the second connection part according to one embodiment of the present invention.
Figure 4:
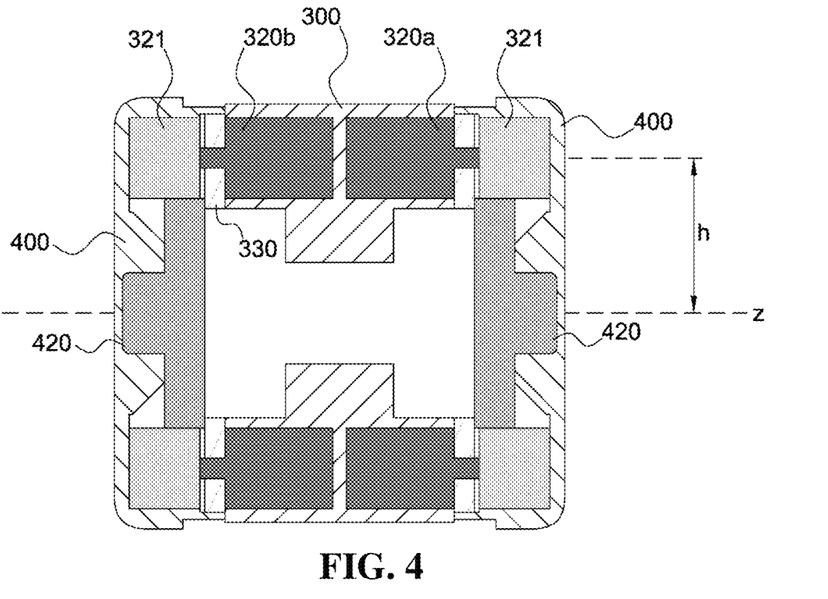
FIG. 4 is a cross-sectional view illustrating the first connection part and the second connection part according to one embodiment of the present invention.
Figure 5:
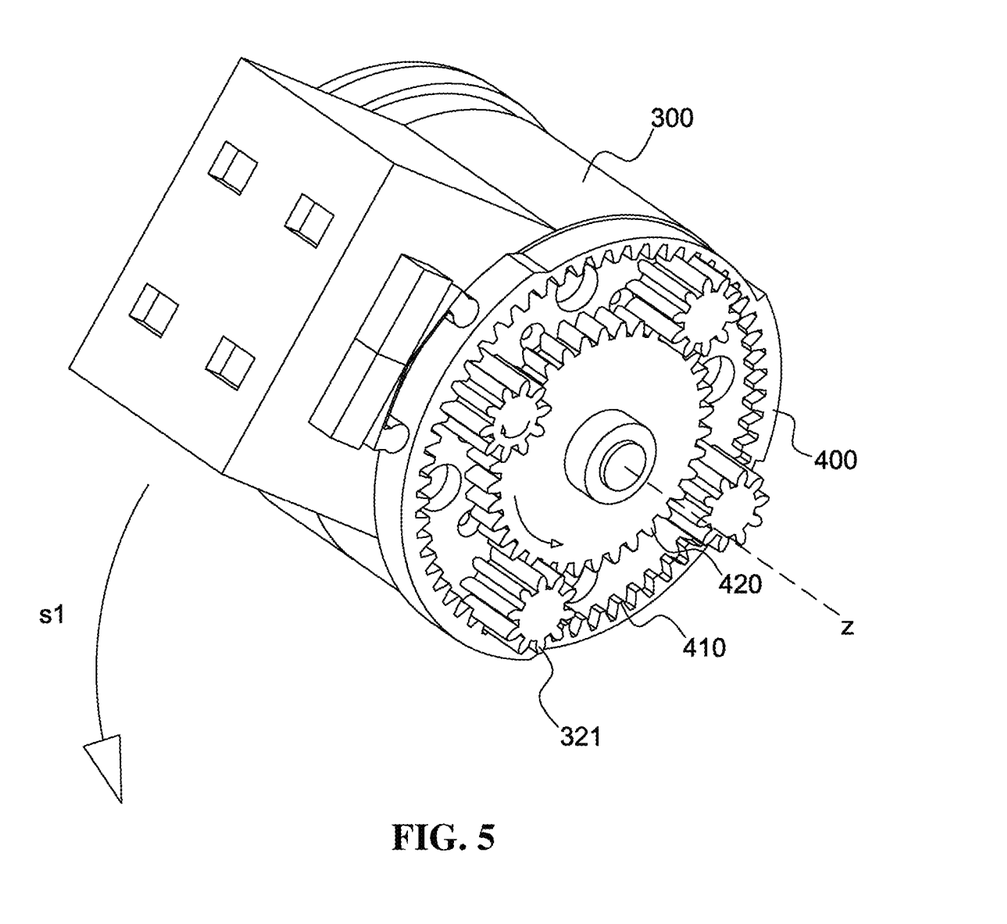
FIG. 5 is a view illustrating a joint motion of the first connection part according to one embodiment of the present invention.

FIG. 2 is a view illustrating a first connection part 300 and a second connection part 400 according to one embodiment of the present invention, FIG. 3 is a view illustrating the first connection part 300 and the second connection part 400 according to one embodiment of the present invention, FIG. 4 is a cross-sectional view illustrating the first connection part 300 and the second connection part 400 according to one embodiment of the present invention.

In order to solve the problems of the configuration of the related art, the present invention discloses the first connection part 300 and the second connection part 400. In detail, the elbow for an electronic prosthetic hand according to the related art uses a plurality of connection units formed in a bar shape to jointly move the upper arm 100 and the lower arm 200. However, there is a problem in that the plurality of connection units are easily bent or damaged by the load of a heavy object when gripping and transporting the heavy object. In detail, when lifting up an object located below the electronic prosthetic hand while gripping the object, the stress applied to the elbow part of the electronic prosthetic hand is determined by multiplying a distance between one end and the other end of the lower arm 200 by the weight of the object. Here, in a tall person, the length of the lower arm 200 required to correspond thereto is large, and thus the magnitudes of the rotational moment and the stress according to the rotation of the elbow part increase, which is a major factor in significantly increasing the probability that the elbow part is overloaded and thus damaged. Further, in contrast to moving the one end of the lower arm 200 in the downward direction to move the gripped object in the downward direction, moving the object in the upward direction increases the height from the ground to the object, and thus the object should be gripped and supported with a greater force. The above-described electronic prosthetic hand according to the related art has a problem in that it is difficult to lift up the object in the above situation. Although there is a method of rotating the lower arm 200 by a separate driving unit, a high-output driving unit is required for the method, and the size of the high-output driving unit is large. Thus, it is difficult for the high-output driving unit to be installed in the elbow part of the electronic prosthetic hand. Accordingly, the present invention discloses an elbow for an electronic prosthetic hand which may easily lift up an object, may be prevented from being damaged, and may replace a large-sized driving unit to eliminate the repulsion of a person.

The first connection part 300 is connected to the lower arm 200 and jointly moves the upper arm 100 and the lower arm 200 by power produced by a driving unit 320. In detail, in a state in which one end of the first connection part 300 is connected to the other end of the lower arm 200, a gear 321 connected to the driving unit 320 is rotated while being engaged with a toothed part 410 of the second connection part 400 which will be described below, and thus the upper arm 100 and the lower arm 200 are jointly moved. That is, the first connection part 300 is configured to connect the upper arm 100 and the lower arm 200, and at the same time, allow the lower arm 200 to perform the first rotational movement s1 and the second rotational movement s2. To this end, one end of the first connection part 300 is connected to the lower arm 200. In detail, the first connection part 300 has a  shape when viewed from the one side surface direction toward the other side surface direction. In detail, a part facing the left side in the  cross-sectional shape, which is one end of the first connection part 300, is connected to the lower arm 200. Further, a part facing the right side in the  cross-sectional shape corresponds to the other end of the second connection part 400. Accordingly, in a state of being connected to the lower arm 200, the first connection part 300 may perform the first rotational movement s1 and the second rotational movement s2 in response to the connection and the rotational movement between the gear 321 connected to the driving unit 320, which will be described below, and the toothed part 410. Further, the cross-sectional shape of the first connection part 300 as described above in the present invention is not limited, and one end thereof may be formed in various shapes such as an arc shape to be firmly connected to the lower arm 200.

An insertion groove 310 is provided in the first connection part 300. The insertion groove 310 provides a space in which the driving unit 320, which will be described below, is to be located. To this end, the insertion groove 310 is formed on one side surface of the first connection part 300. In detail, the insertion groove 310 is formed to be open from one side surface to the other side surface of the first connection part 300. Due to the engraved insertion groove 310 as described above, the driving unit 320 may be easily disposed and may easily supply power to the gear 321 in a state of being inserted into the insertion groove 310, and thus the first rotational movement s1 and the second rotational movement s2 of the lower arm 200 may easily and ultimately be achieved. Further, a plurality of insertion grooves 310 are provided. This is for easily achieving output for the rotational movement of the lower arm 200 as a plurality of driving units 320 are inserted and driven at the same time. It is preferable that the plurality of insertion grooves 310 formed to correspond to the plurality of driving units 320 as described above should be provided to correspond to the shape and the size of the driving units 320. As described with reference to FIG. 2, the plurality of driving units 320 are formed in a rectangular parallelepiped shape, and the insertion grooves 310 are formed to correspond to the size of the driving units 320 so that the inserted driving units 320 do not escape to the outside of the first connection part 300. In an additional exemplary embodiment, the plurality of insertion grooves 310 are provided to have a circular arrangement. In detail, the plurality of insertion grooves 310 are arranged on the concentric circle spaced a predetermined interval h from the one central axis z in an outward direction (see FIG. 4). In more detail, the plurality of insertion grooves 310 are located on the concentric circle and are formed to be spaced apart from each other to have a predetermined arc interval, and the predetermined arc interval is the same between the plurality of insertion grooves 310. Accordingly, the driving unit 320 inserted into the insertion groove 310 may rotate the gear 321, which will be described below, with a uniform force and thus may prevent a stuttering phenomenon during the movement of the lower arm 200 performing the first rotational movement s1 and the second rotational movement s2. That is, as the insertion grooves 310 are formed, the driving units 320 may be more firmly arranged. Thus, the gear 321, which will be described below, may easily rotate without shaking, thereby significantly increasing the stability of the joint movement of the upper arm 100 and the lower arm 200.

In an additional exemplary embodiment, the plurality of the insertion grooves 310 may be formed on the other side surface of the first connection part 300. In detail, the plurality of insertion grooves 310 formed on the other side surface of the first connection part 300 are provided to have the same circular arrangement as the insertion grooves 310 formed on the one side surface of the first connection part 300 and are formed to correspond to the size and shape of the driving units 320. Here, the plurality of insertion grooves 310 provided on the one side surface and the other side surface of the first connection part 300 are sequentially arranged so that internal spaces are not joined to each other. That is, the insertion grooves 310 are provided so that the plurality of driving units 320 inserted into the one side surface and the other side surface of the first connection part 300 are not in contact with each other. As an example, when the first connection part 300 is viewed from the one side surface direction to the other side surface direction, the driving unit 320 provided on the one side surface of the first connection part 300 is located between a pair of driving units 320 provided on the other side surface. Therefore, the plurality of gears 321 rotating while being respectively connected to the plurality of driving units 320 may have a uniform output, and at the same time, may be prevented from being damaged by coming in contact with each other. Further, more driving units 320 may be accommodated as compared to a case in which the insertion grooves 310 are provided only on the one side surface direction of the first connection part 300. This reduces the output of the respective driving units 320 required to jointly move the upper arm 100 and the lower arm 200 to significantly reduce noise or to easily grip and transport a heavy object.

The driving units 320 are configured to finally realize a joint motion between the upper arm 100 and the lower arm 200 by rotating the gear 321 which will be described below. To this end, the driving units 320 may be provided as a driving unit such as a motor, which is driven by receiving power from a separate battery or the like and has one end formed in a rod shape. Further, the driving units 320 are inserted and located in the insertion grooves 310. In detail, the driving units 320 are formed to correspond to the size and the shape of the insertion grooves 310 formed on the one side surface and the other side surface of the first connection part 300. Accordingly, the driving units 320 may be prevented from being separated from the plurality of insertion grooves 310 formed on the one side surface and the other side surface of the first connection part 300 while being in a state of being inserted into the insertion grooves 310. This may lead to an effect of preventing the distortion of one end of the driving unit 320, which is connected to the gear 321 and formed in a rod shape. Further, the plurality of driving units 320 are divided and classified into a first driving group 320a and a second driving group 320b. In detail, the plurality of driving units 320 are classified into the first driving group 320a including the plurality of driving units 320 located in the one side surface direction (referring to a rightward direction in FIG. 4) with respect to the first connection part 300 and the second driving group 320b including the plurality of driving units 320 provided in the other side surface direction (referring to a leftward direction in FIG. 4). In this way, the plurality of driving units 320, which are classified into the first driving group 320a and the second driving group 320b, may be driven for each group to produce a more uniform output, thereby rotating the gears 321 connected to the one ends thereof. That is, since the first driving group 320a and the second driving group 320b are provided, the lower arm 200 and the upper arm 100 may be easily jointly moved, a person wearing the electronic prosthetic hand is prevented from feeling uncomfortable, and thus convenience can be increased.

The gear 321 is provided at the one end of the driving unit 320. In a state of being engaged with the toothed part 410, which will be described below, the gear 321 is rotated by the driving unit 320 to jointly move the upper arm 100 and the lower arm 200. To this end, the gear 321 is formed in a shape of a spur gear and is connected to the one end of the driving unit 320 formed in the shape of a rod. Further, the outer peripheral surface of the gear 321 is engaged with the toothed part 410 and a support gear 321 provided in the second connection part 400, which will be described below. Accordingly, the gear 321 performs the first rotational movement s1 and the second rotational movement s2 along the toothed part 410 while being rotated by the driving unit 320, and thus may adjust the angle between the lower arm 200 and the upper arm 100. A more detailed description thereof will be described after the toothed part 410 and the support gear 420 are described.

The second connection part 400 is configured to rotate the gear 321 provided in the first connection part 300 so as to cause the lower arm 200 to perform the first rotational movement s1 and the second rotational movement s2. To this end, one end of the second connection part 400 facing the rear side is fixedly connected to the upper arm 100, and the other end thereof located in front of the upper arm 100 is formed to have a circular cross-sectional shape. Further, the other end of the second connection part 400 is located in the one side surface direction and the other side surface direction of the first connection part 300. Further, the toothed part 410, which is engaged with the gear 321 to rotate the gear 321 as described above, is provided at the other end of the second connection part 400. In detail, in a state in which the one end of the second connection part 400 is fixedly connected to the upper arm 100, while the gears 321 connected to the plurality of driving units 320 are engaged with the toothed part 410, the one end of the second connection part 400 is rotated along the toothed part 410, and thus the lower arm 200 may be rotated.

The toothed part 410 provides a path so that the gear 321 as described above performs the first rotational movement s1 and the second rotational movement s2 by the driving unit 320. In detail, the path is provided so that the gear 321 rotates while being engaged with the toothed part 410 located in an outward direction of the gear 321. To this end, the toothed part 410 is provided inside the second connection part 400. In detail, the toothed part 410 is formed on the inner surface of the second connection part 400. In more detail, the toothed part 410 is formed so that a plurality of teeth are arranged in a circular shape and is arranged to face the inner side with respect to the one central axis z. Accordingly, the toothed part 410 is formed in the plurality of gears 321 in the outward direction. Further, the toothed part 410 is fixedly provided in the second connection part 400 fixedly connected to the upper arm 100. Accordingly, in a state of being engaged with the toothed part 410, the gear 321 is rotated by the driving unit 320 to perform the first rotational movement s1 and the second rotational movement s2 about the one central axis z. To this end, it is preferable that the toothed part 410 is engaged with the gear 321. Further, as the second connection part 400 is provided on the first connection part 300 in the one side surface direction and the other side surface direction, the toothed part 410 is also provided in the first connection part 300 in the one side surface direction and the other side surface direction. In detail, the toothed part 410 is divided into a first tooth part 410a located in the one side surface direction of the first connection part 300 and provided at the first connection part 300 and a second tooth part 410b located in the other side surface direction of the first connection part 300 and provided at the first connection part 300. Thus, the first tooth part 410a and the second tooth part 410b are engaged with the gear 321 connected to the first driving group 320a and the second driving group 320b located in both side surface directions of the first connection part 300, and the gear 321 is rotated about the one central axis z along the first tooth part 410a and the second tooth part 410b while being rotated by the driving unit 320, and thus the lower arm 200 may perform the first rotational movement s1 and the second rotational movement s2.

The second connection part 400 further includes a first fastening groove 401. The first fastening groove 401 is configured so that the support gear 420, which will be described below, may easily rotate about the one central axis z in a state of being fixed to the inside of the second connection part 400. To this end, the first fastening groove 401 is engraved from one side surface to the other side surface of the second connection part 400. When an example of the second connection part 400 located in the one side surface direction of the first connection part 300 is described, the first fastening groove 401 is formed by being open from one side of the second connection part 400 facing the one side surface direction. Here, as a first protrusion 421 provided in the support gear 420, which will be described below, is inserted into the first fastening groove 401, the support gear 420 may be located inside the second connection part 400 and located in an inner direction of the first tooth part 410a. The first fastening groove 401 is provided, the first protrusion 421 is inserted into the first fastening groove 401, and thus the support gear 420 is located in the inner direction of the toothed part 410. Thus, the gear 321 may more easily rotate by the support gear 420 located in the inner direction.

The support gear 420 supports the gear 321 so that the gear 321 easily rotates. In detail, the support gear 420 is located in the inner direction of the gear 321, and thus the gear 321 is easily rotated while being engaged with the support gear 420. To this end, the support gear 420 is provided in the second connection part 400. In detail, the support gear 420 is provided inside the second connection part 400 located at both side surfaces of the first connection part 300, and the first protrusion 421 located in the one side surface direction and the other side surface direction of the support gear 420 is located to be inserted into the first fastening groove 401 provided in the second connection part 400 described above. Accordingly, the plurality of gears 321 and the toothed part 410 are located in the outward direction of the support gear 420, and the gears 321 are located between the toothed part 410 and the support gear 420 and are engaged with each other. Further, a central axis z of the support gear 420 coincides with the one central axis z. Accordingly, the support gear 420 rotates about the one central axis z. When an example in which the lower arm 200 performs the first rotational movement s1 (see FIG. 9) is described, the gear 321 performs the second rotational movement s2 by driving the driving unit 320, and the support gear 420 performs the first rotational movement s1 to correspond to the above-described rotational movement of the gear 321. That is, the support gear 420 is engaged with the gear 321 located in the outward direction and rotates in a direction opposite to the rotation direction of the gear 321 so that the gear 321 is easily rotated. Further, the gear 321 is in a fixed state and moves with the one central axis z as a center along the toothed part 410 located in the outward direction. Accordingly, the lower arm 200 connected to the first connection part 300 performs the first rotational movement s1.

The upper arm 100 and the lower arm 200 may be easily jointly moved according to the structure in which the gear 321, the toothed part 410, and the support gear 420 are engaged with each other and the rotation of the gear 321 and the support gear 420 according to the driving of the driving unit 320. Further, as the plurality of driving units 320 generating low noise during the driving process are provided and located, excessively loud noise can be prevented from occurring while the lower arm 200 performs the first rotational movement s1 and the second rotational movement s2, and thus discomfort of the person wearing the electronic prosthetic hand can be prevented. Further, even when a problem occurs that any one driving unit 320 among the plurality of driving units 320 is not driven, the remaining driving units 320 are driven to rotate the gear 321, and thus malfunctions that occur during the joint movement of the upper arm 100 and the lower arm 200 can be minimized. In addition, since the plurality of driving units 320 are provided, the high-output driving unit may be replaced, and thus manufacturing costs can be dramatically reduced, and the elbow part of the electronic prosthetic hand can be prevented from being enlarged. Therefore, repulsion of the user can be minimized which is generated in a process of wearing the electronic prosthetic hand and in daily life.

A plate part 330 is configured to support a gear shaft of the driving unit 320. In detail, the plate part 330 prevents the one end of the driving unit 320 formed in a rod shape from being twisted during the rotation process, thereby ultimately making the first rotational movement s1 and the second rotational movement s2 of the gear 321 easy. To this end, the plate part 330 is provided in a plate shape, located in both side surface directions of the first connection part 300, and located between the first connection part 300 and the second connection part 400. In detail, plate parts 330 are located at the first connection part 300 but provided in a pair and are arranged in the one side surface direction and the other side surface direction of the first connection part 300.

The plate part 330 includes a distortion prevention part 331 formed to correspond to the gear shaft (referring to the one end of the driving unit 320 formed in a rod shape) of the driving unit 320. A plurality of distortion prevention parts 331 are provided and are open to pass through the plate part 330. Accordingly, the one end of the driving unit 320 is connected to the gear 321 in a state of being inserted through the distortion prevention part 331, and the gear 321 is located in a direction opposite to the driving unit 320 with respect to the plate part 330. Thus, while the gear 321 is rotated by driving the driving unit 320, the gear shaft of the driving unit 320 can be prevented from being twisted or the gear 321 can be prevented from unintentionally escaping in the one side surface direction and the other side surface direction. Further, the support gears 420 located in both side surface directions of the first connection part 300 are located in the one side surface direction and the other side surface direction of the plate part 330 in a state in which the first protrusion 421 is inserted into the first fastening groove 401 and is located inside the second connection part 400. Thus, the support gears 420 may be prevented from escaping from the inside of the second connection part 400, and thus the gear 321 may be ultimately and more firmly supported and rotated.

In an additional exemplary embodiment, the plate part 330 further includes a through groove 332. The through groove 332 allows an arrangement part 340 provided by winding a spiral spring 350, which will be described below, to pass through the plate part 330 and to be fastened to the support gear 420. To this end, the through groove 332 is formed in the plate part 330, and the diameter of the through-groove 332 is greater than the diameter of the arrangement part 340. Accordingly, the arrangement part 340 passes through the plate part 330 and is fixedly fastened to the support gear 420, the support gear 420 and the arrangement part 340 integrally perform the first rotational movement s1, and thus the spiral spring 350 may be wound. A more detailed description of the process of winding the spiral spring 350 will be made below with reference to FIGS. 6 to 9.

Figure 6:
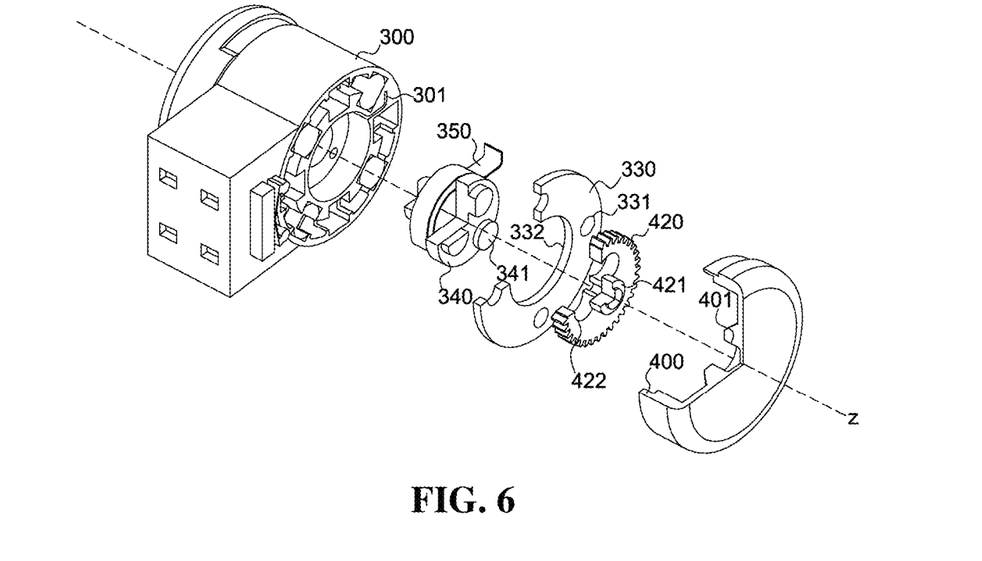
FIG. 6 is a cut-away perspective view illustrating a support gear and a spiral spring according to one embodiment of the present invention.
Figure 7:
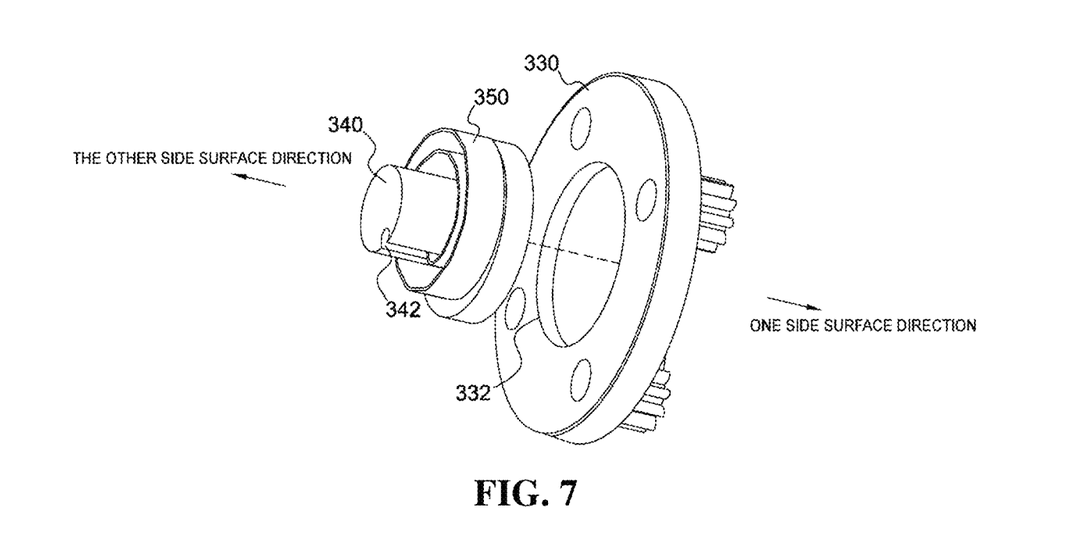
FIG. 7 is a view illustrating the support gear and the spiral spring according to one embodiment of the present invention.

FIG. 6 is a cut-away perspective view illustrating a support gear 420 and a spiral spring 350 according to one embodiment of the present invention, and FIG. 7 is a view illustrating the support gear 420 and the spiral spring 350 according to one embodiment of the present invention. FIG. 6 illustrates a cross section obtained by cutting the arrangement part 340, the plate part 330, the support gear 420, and the second connection part 400 provided in the one side surface direction of the first connection part 300 to illustrate the fastening and fixation of the arrangement part 340 and the support gear 420 and the insertion and fixing of the first protrusion 421 of the support gear 420 and the first fastening groove 401.

A first fixing groove 301 is configured to position the spiral spring 350, which will be described below, inside the first connection part 300. To this end, first fixing grooves 301 are formed in the one side surface and the other side surface of the first connection part 300 and are formed to correspond to the shape of the spiral spring 350 so that one end of the spiral spring 350 is inserted thereinto. In detail, the first fixing grooves 301 are provided to be bent in an "L" shape and are engraved from the one side surface and the other side surface of the first connection part 300, and the one end of the spiral spring 350 is connected to the first connection part 300 by being inserted into and located in the first fixing grooves 301. Since the first fixing groove 301 having a cross-sectional shape bent in an "L" shape is provided, the spiral spring 350 is firmly located in a state in which the one end thereof is inserted into the first fixing groove 301. Thus, since the spiral spring 350 does not escape from the inside of the first connection part 300, a force consumed while the lower arm 200 is bent by performing the second rotational movement s2 may be compensated for, and thus, an overload of the driving unit 320 may be prevented from occurring when lifting up a heavy object. In particular, when the spiral spring 350 is wound, one end of the first fixing groove 301 provided to be bent in an "L" shape is continuously and easily maintained in a fixed state.

The arrangement part 340 positions the spiral spring in the first connection part 300 and serves to wind or unwind the spiral spring 350 in response to the rotational movement of the gear 321. To this end, one end of the arrangement part 340 is provided in a disk shape and passes through the through groove 332 described above, and the spiral spring 350 is wound and located on the other end thereof. In detail, the arrangement part 340 has the one end facing the second connection part 400 and the other end facing the first connection part 300, which are formed in a disk shape and a rod shape, respectively, and the diameter of the one end is greater than the diameter of the other end. Therefore, while the spiral spring 350 is wound or unwound, the spiral spring 350 may be prevented from escaping toward the second connection part 400 by being blocked by the one end of the arrangement part 340. In an additional exemplary embodiment, a second protrusion 341 for fastening and fixing with the support gear 420 may further provided in the one end of the arrangement part 340. In detail, second protrusions 341 are provided in a disc shape, are provided in plural, and are located to have a circular arrangement about the one central axis z. In addition, second fastening grooves 422, into which the second protrusions 341 are inserted to integrally rotate the arrangement part 340 and the support gear 420, are further provided in the one side surface and the other side surface of the support gear 420 facing the first connection part 300. In detail, the second fastening grooves 422 are provided in the other side surface of the support gear 420 located in the one side surface direction of the first connection part 300 and in the one side surface of the support gear 420 located in the other side surface direction of the first connection part 300. The second fastening groove 422 is provided to have the same diameter as the diameter of the second protrusion 341 to prevent the second protrusion 341 from escaping from the inserted state. As described above, the arrangement part 340 rotates integrally with the support gear 420 as the second protrusion 341 is located to be inserted into the second fastening groove 422, and the spiral spring 350 may be bent or unfolded in response to the rotation of the support gear 420. A more detailed description of a process of bending or unfolding the spiral spring 350 will be made below with reference to FIG. 8.

A second fixing groove 342 for inserting and fixing the other end of the spiral spring 350 is further provided at the other end of the arrangement part 340. Similar to the first fixing groove 301, the second fixing groove 342 functions to fix the spiral spring 350 so that the spiral spring 350 does not escape while the spiral spring 350 is bent or unfolded. To this end, the second fixing groove 342 is engraved from the outer peripheral surface of the other end of the arrangement part 340, and the other end of the spiral spring 350 is fixedly inserted into the second fixing groove 342. Therefore, in a state in which the one end and the other end of the spiral spring 350 are inserted into and fixed to the first fixing groove 301 and the second fixing groove 342, respectively, the support gear 420 is bent by the first rotational movement s1 or is unfolded by the second rotational movement s2. Thus, the lower arm 200 may be prevented from excessively performing the first rotational movement s1, and a force consumed while the lower arm 200 performs the second rotational movement s2 may be assisted.

The spiral spring 350 is configured to compensate for a force consumed when the lower arm 200 rotates. In detail, the spiral spring 350 reduces the output of the driving unit 320 required when the lower arm 200 is lifted up in a state in which the upper arm 100 and the lower arm 200 are collinearly located, and thus the spiral spring 350 prevents an overload of the driving unit 320. To this end, the spiral spring 350 is provided to have a restoring force. In detail, the spiral spring 350 is provided to be unfolded using the restoring force in a bent state. Further, the one end of the spiral spring 350 is inserted into the first fixing groove 301, the other end thereof is inserted into the second fixing groove 342, and thus both ends of the spiral spring 350 are fixed. As described above, in a state in which the spiral spring 350 is fixed, the support gear 420 moving integrally with the arrangement part 340 performs the first rotational movement s1 while being engaged with the gear 321, and thus the spiral spring 350 is bent and wound. Further, the wound spiral spring 350 is unfolded using the restoring force as the support gear 420 engaged with the gear 321 performs the second rotational movement s2, may assist the output of the driving unit 320 in this process, and thus may compensate for a force required to bend the upper arm 100 and the lower arm 200. A more detailed description of the compensation of the spiral spring 350 will be made with reference to FIG. 8.

Figure 8:
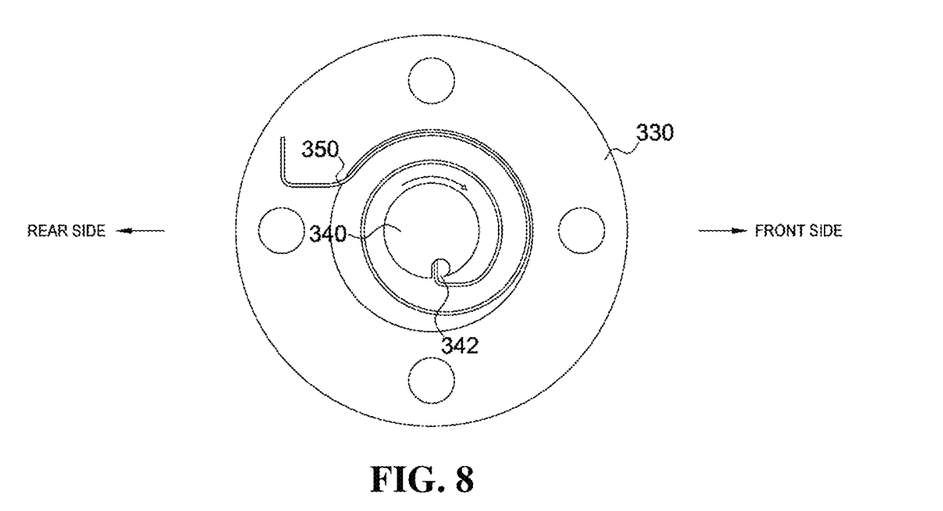
FIG. 8 is a view illustrating a state in which the spiral spring is wound by rotating the support gear according to one embodiment of the present invention.
Figure 9:
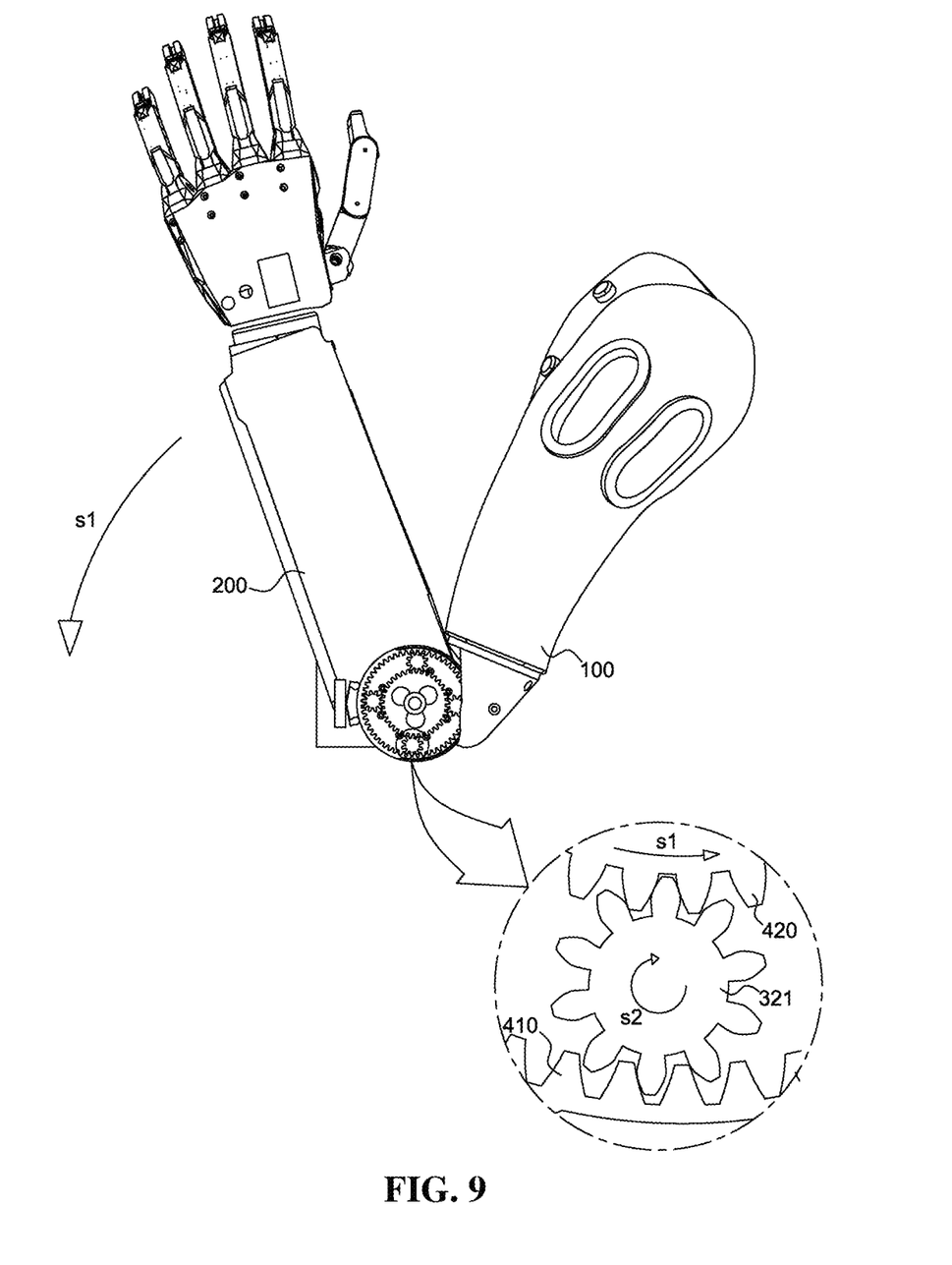
FIG. 9 is a view illustrating a rotational movement of a gear when lowering an upper arm according to one embodiment of the present invention.

FIG. 8 is a view illustrating a state in which the spiral spring 350 is wound by rotating the support gear 420 according to one embodiment of the present invention, and FIG. 9 is a view illustrating a rotational movement of a gear 321 when lowering an upper arm 100 according to one embodiment of the present invention. FIG. 8 illustrates a state in which the spiral spring 350 is wound, and illustrates the plate part 330 in the first connection part 300, the plate part 330 directed toward the second connection part 400, the arrangement part 340, and the spiral spring 350. That is, the rotation of the arrangement part 340 illustrated in FIG. 8, which is the first rotational movement s1, is rotational movement of the arrangement part 340 which is performed when the angle between the upper arm 100 and the lower arm 200 increases as illustrated in FIG. 9.

In a state in which the second protrusion 341 provided in the arrangement part 340 is inserted into the second fixing groove 342 provided in the support gear 420, as illustrated in FIG. 9, as the gear 321 performs the second rotational movement s2 (referring to a clockwise rotation in FIG. 9) along the toothed part 410, the lower arm 200 performs the first rotational movement s1 (referring to a counterclockwise rotation in FIG. 9), and the support gear 420 engaged with the gear 321 performs the first rotational movement s1. Here, the arrangement part 340 moving integrally with the support gear 420 performing the first rotational movement s1 performs the first rotational movement s1 (referring to a clockwise rotation in FIG. 8) as illustrated in FIG. 8. Thus, the spiral spring 350 having one end and the other end fixedly inserted into the first fixing groove 301 and the second fixing groove 342, respectively, is wound in response to the first rotational movement s1 of the arrangement part 340.

On the other hand, when the lower arm 200 is lifted up and the upper arm 100 and the lower arm 200 are bent, the gear 321 performs the first rotational movement s1 (referring to a counterclockwise rotation in FIG. 9) along the toothed part 410, and the support gear 420 engaged with the gear 321 and the arrangement part 340 provided in the support gear 420 perform the second rotational movement s2 (referring to a clockwise rotation in FIG. 8). Here, the spiral spring 350 generates a restoring force, by which the spiral spring 350 is bend and then unfolded, to compensate for the force so that the arrangement part 340 connected to the other end thereof and the support gear 420 fastened to the arrangement part 340 easily perform the second rotational movement s2. Thus, in order to lift up the lower arm 200, the spiral spring 350 may assist the driving unit 320 so that the output to be generated by the driving unit 320 does not become larger, thereby preventing an overload of the driving unit 320. That is, while the lower arm 200 is moved up in a state of gripping the object, as the potential energy increases in accordance with the height of the object being spaced apart from the ground, the output required from the driving unit 320 increases. In this case, by compensating for the force through the restoring force of the spiral spring 350, the driving unit 320 may be prevented from being driven with an excessively large output.

Through the above configuration and effect, the driving unit 320 does not have to be driven with a greater output than when lifting up the object, and thus damage due to overheating can be prevented. Further, since an auxiliary output for easily bending the lower arm 200 is performed not by a driving unit such as a motor but by the restoring force of the spiral spring 350, noise is minimized, the user may not feel discomfort, and thus the quality of a product can be improved. Further, regardless of when the upper arm 100 and the lower arm 200 are collinearly located and when the lower arm 200 is lifted up, the driving unit 320 performs these operations using the same output, and in this case, since a separate control unit for controlling the output of the driving unit 320 may be omitted, the simplification and miniaturization of the electronic prosthetic hand can be easily implemented.

Figure 10:
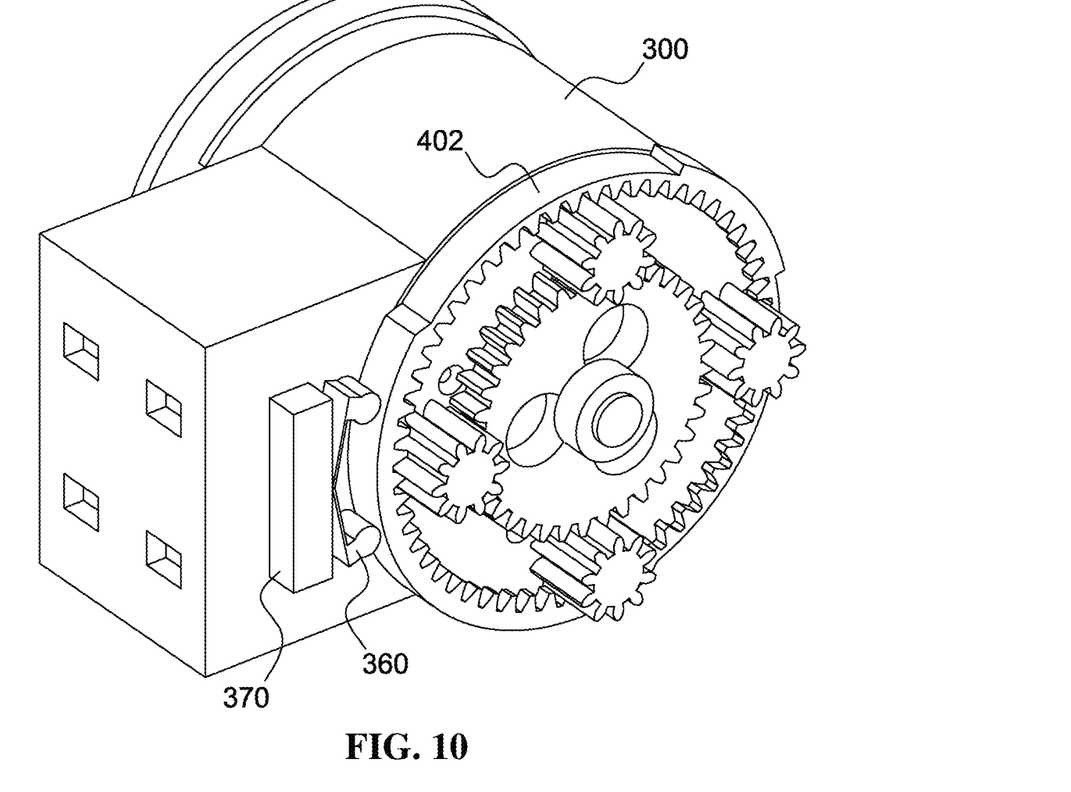
FIG. 10 is a view illustrating an engraved part, a contact part, and a recognition unit according to one embodiment of the present invention.
Figure 11:
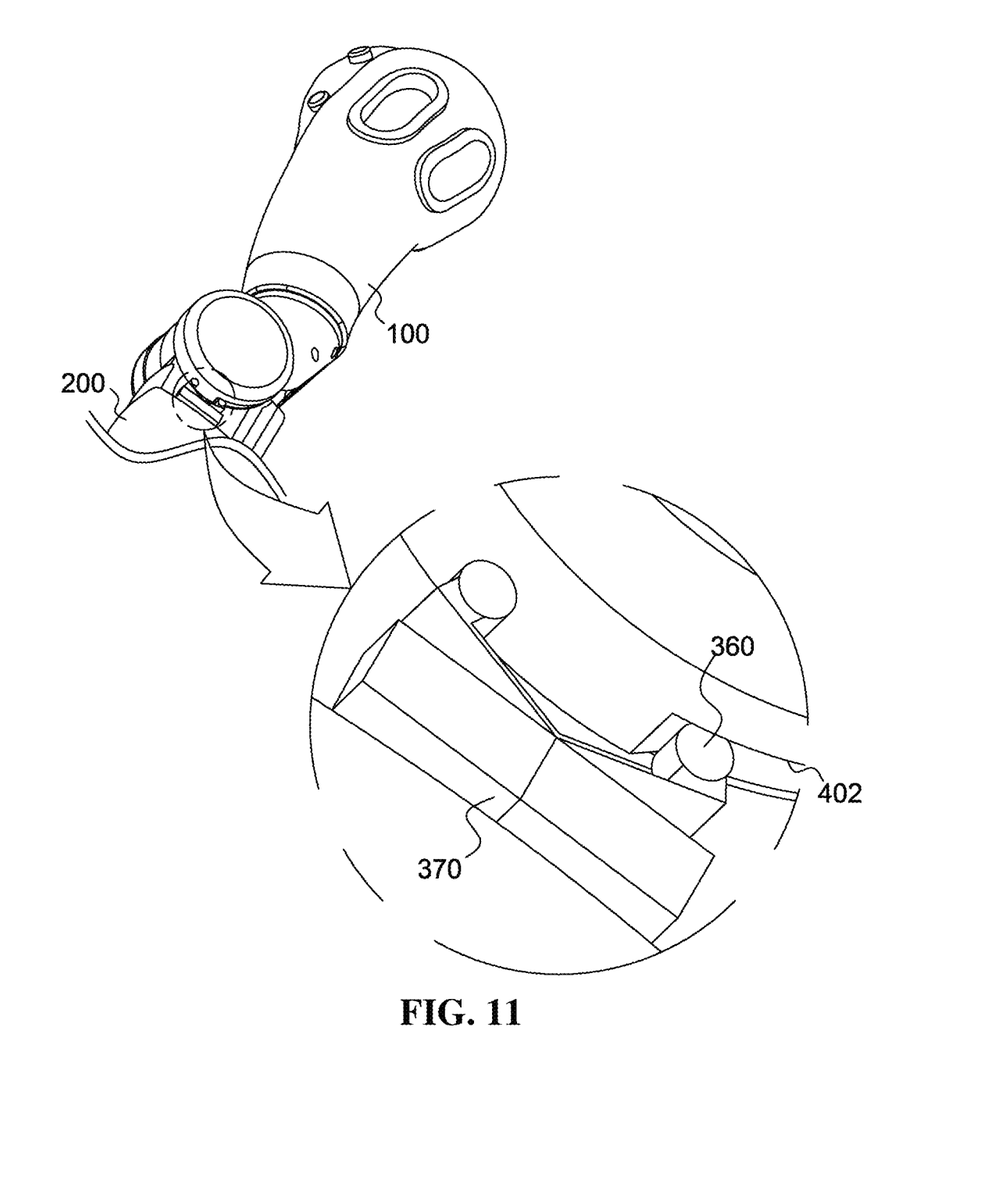
FIG. 11 is a view illustrating a surface contact between the engraved part and the contact part when the upper arm and a lower arm are collinearly arranged according to one embodiment of the present invention.

FIG. 10 is a view illustrating an engraved part 402, a contact part 360, and a recognition unit 370 according to one embodiment of the present invention, and FIG. 11 is a view illustrating a surface contact between the engraved part 402 and the contact part 360 when the upper arm 100 and the lower arm 200 are collinearly arranged according to one embodiment of the present invention. In FIG. 11, in order to easily illustrate the engraved part 402, the contact part 360, and the recognition unit 370, the second connection part 400 is omitted. In FIG. 11, in order to express contact between the engraved part 402 and the recognition unit 370, the engraved part 402 and the contact part 360 are enlargedly illustrated in a state in which the upper arm 100 and the lower arm 200 are collinearly arranged.

In the electronic prosthetic hand according to the related art, the angle between the upper arm 100 and the lower arm 200 is excessively increased while the upper arm 100 and the lower arm 200 jointly move, and thus the bending of the lower arm 200 should be visually identified and controlled. That is, in the case of a user having poor eyesight, as the lower arm 200 is excessively bent, it is difficult to prevent a load concentration phenomenon of the elbow part and damage to the elbow part due to an increase in the load of the object gripped by the lower arm 200. In the present invention, disclosed are the engraved part 402, the contact part 360, and the recognition unit 370 that may solve such a problem.

The engraved part 402 is configured to detect whether or not the upper arm 100 and the lower arm 200 are collinearly arranged, by contacting the contact part 360 which will be described below. In detail, the contact part 360, which will be described below, comes into contact with the engraved part 402, the recognition unit 370 connected to the contact part 360 recognizes this contact, and thus it may be regarded that the upper arm 100 and the lower arm 200 are collinearly arranged. To this end, the engraved part 402 is provided in the second connection part 400. In detail, the engraved part 402 is provided in the second connection part 400 in an outward direction and engraved from the second connection part 400 to a predetermined depth. Here, when the upper arm 100 and the lower arm 200 are collinearly located, the engraved part 402 is formed to be in surface contact with the contact part 360. In detail, the engraved part 402 is maintained in a fixed state without moving in a state of being provided in the second connection part 400, and the contact part 360, which will be described below, integrally moves in response to the first rotational movement s1 and the second rotational movement s2 of the lower arm 200, and comes into surface contact with the engraved part 402 when the upper arm 100 and the lower arm 200 are collinearly located and the one end of the lower arm 200 is thus directed to the front side. Therefore, the recognition unit 370 may detect the arrangement state of the upper arm 100 and the lower arm 200 by recognizing the surface contact between the engraved part 402 and the contact part 360. To this end, it is preferable that when the upper arm 100 and the lower arm 200 are collinearly located, the position of the engraved part 402 should be determined so that the contact part 360 and the engraved part 402 come into contact with each other. In detail, the engraved part 402 is provided in a lower direction of the second connection part 400, and thus comes into surface contact with the contact part 360 moving integrally with the lower arm 200 though the first rotational movement s1.

As still another embodiment of the present invention, the engraved part 402 may further provided in an upper direction of the second connection part 400. This is for preventing the lower arm 200, in which the angle between the lower arm 200 and the upper arm 100 is reduced, from excessively approaching the upper arm 100. In detail, when the engraved part 402 further provided at the upper side of the second connection part 400 is maintained in a fixed state and when the contact part 360 provided in the first connection part 300 performs the second rotational movement s2 about the one central axis z in response to the second rotational movement s2 of the lower arm 200, the contact part 360 moves to, is inserted into, and comes in surface contact with the engraved part 402 located in the upper direction of the second connection part 400, and the recognition unit 370 may detect this insertion and surface contact to determine that the upper arm 100 and the lower arm 200 are located in a bent state.

The contact part 360 may allow the recognition unit 370, which will be described below, to identify an arrangement state of the upper arm 100 and the lower arm 200 by performing the surface contact with the engraved part 402. To this end, contact parts 360 are provided in the one side surface direction and the other side surface direction of the first connection part 300 and are located in front of the second connection part 400. Further, the contact part 360 has a "<" cross-sectional shape in which both ends thereof are provided to face the upper direction and the lower direction of the second connection part 400. Thus, both ends of the contact part 360 move along the outer peripheral surface of the second connection part 400 in accordance with the first rotational movement s1 and the second rotational movement s2 of the lower arm 200 about the one central axis z. In an additional exemplary embodiment, as separate rollers are further provided at both ends of the contact part 360, the contact part 360 may more easily move along the outer peripheral surface of the second connection part 400. Further, the contact part 360 is connected to the recognition unit 370. In detail, the recognition unit 370, which will be described below, is provided in the first connection part 300, is located in front of the contact part 360, and is connected to both ends of the contact part 360. Here, the contact part 360 and the recognition unit 370 may be connected to a separate elastic part formed as a spring or the like. In detail, the recognition unit 370 is connected to the contact part 360 through the elastic part, identifies that the contact part 360 and the engraved part 402 are in surface contact with each other when it is detected through a separate sensor unit that the elastic part is stretched, and thus considers that the upper arm 100 and the lower arm 200 are collinearly located. Both ends of the contact part 360 moving with the one central axis z as a center toward the upper direction and the lower direction of the second connection part 400 along the outer peripheral surface of the second connection part 400 are in surface contact with the engraved part 402 maintained in a fixed state. Here, the engraved part 402 formed by being engraved in the one central axis z direction from the outer peripheral surface of the second connection part 400 has a step difference as much as a predetermined depth with respect to the outer peripheral surface of the second connection part 400, and as the distance between both ends of the contact part 360 in surface contact with the engraved part 402 and the recognition unit 370 increases, the recognition unit 370 recognizes the contact between the engraved part 402 and the contact part 360. In an additional exemplary embodiment, the recognition unit 370 has independent sensor units at both ends of the contact part 360 facing the upper direction and the lower direction of the second connection part 400, the sensor units are provided as a relay sensor or the like, and the sensor units may detect an increase in the distance between both ends of the contact part 360 and the recognition unit 370, thereby inferring the positions of the upper arm 100 and the lower arm 200, Further, the recognition unit 370 is connected to a separate notification unit and may notify the user of collinearity through light, sound, or the like when the upper arm 100 and the lower arm 200 are formed collinearly. Thus, the first connection part 300 and the second connection part 400 may be prevented from being damaged by excessively bending the lower arm 200.

Hereinafter, as an example of FIG. 1, the position recognition of the lower arm 200 and the upper arm 100 of the recognition unit 370 according to the contact between the engraved part 402 and the contact part 360 will be described.

In order for the upper arm 100 and the lower arm 200 to be collinearly located, as the lower arm 200 performs the first rotational movement s1, the contact part 360 performs the first rotational movement s1 about the one central axis z along the outer peripheral surface of the second connection part 400. As illustrated in FIG. 11, when the upper arm 100 and the lower arm 200 are collinearly arranged, one end facing the lower direction of the second connection part 400 among both ends of the contact part 360 comes into surface contact with the engraved part 402 engraved to a predetermined depth away from the outer peripheral surface of the second connection part 400. In detail, the contact part 360 is in contact with the engraved part 402 formed to be stepped with the outer peripheral surface of the second connection part 400. Accordingly, the distance between the recognition unit 370 and the one end of the contact part 360 in surface contact with the engraved part 402 is increased as compared to the distance between the recognition unit 370 and the other end of the contact part 360. Accordingly, the recognition unit 370 recognizes, through the separate sensor unit, the one end of the contact part 360 greatly spaced apart from the recognition unit 370, and thus determines that the upper arm 100 and the lower arm 200 are formed collinearly. That is, the recognition unit 370 recognizes the collinearity only in a situation in which the upper arm 100 and the lower arm 200 are collinearly located. Thus, the user may recognize the upper arm 100 and the lower arm 200 before the lower arm 200 is bent by additionally performing the first rotational movement s1 after the upper arm 100 and the lower arm 200 are arranged in a "-" shape, and thus an excessive load can be prevented from being applied to the first connection part 300 and the second connection part 400. Through the above configurations and functions, a situation in which the user feels discomfort that may occur when the lower arm 200 and the upper arm 100 are excessively bent can be prevented. Further, when the one end of the lower arm 200 grips the object, a larger rotational moment and a larger stress may be prevented from acting on the elbow part of the electronic prosthetic hand. Thus ultimately, damage to the electronic prosthetic hand can be prevented.

The above-described exemplary embodiments of the present invention have been disclosed for purposes of illustration, those skilled in the art to which the present invention pertains can deduce various modifications, changes, and additions without departing from the spirit and scope of the present invention, and it should be understood that such modifications, changes, and additions belong to the scope of the appended claims.

Since those skilled in the art to which the present invention pertains can deduce various substitutions, modifications, and changes without departing from the technical spirit of the present invention, the present invention is not limited by the above-described embodiments and the accompanying drawings.

DESCRIPTION OF REFERENCE NUMERALS

| | |
|---|---|
| 100: | Upper arm |
| 200: | Lower arm |
| 300: | First connection part |
| 301: | First fixing groove |
| 310: | Insertion groove |
| 320: | Driving unit |
| 321: | Gear |
| 330: | Plate part |
| 331: | Distortion prevention part |
| 332: | Through groove |
| 340: | Arrangement part |

-continued

| | |
|---|---|
| 341: | Second protrusion |
| 342: | Second fixing groove |
| 350: | Spiral spring |
| 360: | Contact part |
| 370: | Recognition unit |
| 400: | Second connection part |
| 401: | First fastening groove |
| 410: | Toothed part |
| 420: | Support gear |
| 421: | First protrusion |
| 422: | Second fastening groove |

The invention claimed is:

1. An elbow structure of an electronic prosthetic hand in which an upper arm and a lower arm are hinge-connected and which jointly moves the upper arm and the lower arm about one central axis z, the elbow structure comprising:

a first connection part that has one end connected to the lower arm and is provided with a plurality of driving units disposed on a concentric circle spaced a predetermined interval (h) from the one central axis (z) in another end thereof and provided with gears; and a second connection part that has one end connected to the upper arm and has a toothed part disposed in a circular shape to be engaged with the gears of the plurality of driving units in an outward direction and rotated therewith, wherein the gears of the plurality of driving units are rotated while being engaged with the toothed part, wherein the toothed part is provided in a pair and includes a first toothed part located in one side surface direction with respect to the first connection part and a second toothed part located in another side surface direction, wherein the plurality of driving units are classified into a first driving group facing the one side surface direction so that the gears are engaged with the first toothed part and a second driving group facing the another side surface direction so that the gears are engaged with the second toothed part, and wherein the first driving group and the second driving group are arranged sequentially with each other.

2. The elbow structure of claim 1, comprising a support gear (420) that is provided in the second connection part, rotates about the central axis (z), and supports the gears of the plurality of driving units by being engaged with the gears of the driving units.

3. The elbow structure of claim 1, comprising a spiral spring that has one end connected to the first connection part and the other end connected to the support gear, wherein, when an operation of unfolding an elbow is performed such that the upper arm and the lower arm are collinearly located, the spiral spring is wound by the support gear, and when an operation of bending the upper arm and the lower arm is performed, the spiral spring is unfolded by a restoring force, and thus a force required for bending the upper arm and the lower arm is compensated for.

4. The elbow structure of claim 3, wherein further comprising a plate part that is provided in the first connection part, has a distortion prevention part formed to correspond to a gear shaft of the driving unit, and supports the gear shaft.

5. The elbow structure of claim 1, further comprising:

an engraved part that is formed in the second connection part in an outward direction and engraved to a predetermined depth;

contact parts that are formed on the first connection part in the one side surface direction and the another side surface direction and are in surface contact with the engraved part when the upper arm and the lower arm are collinearly arranged; and a recognition unit that is connected to the contact part and detects an arrangement in which the upper arm and the lower arm are collinearly arranged when the engraved part and the contact part are in contact with each other.

* * * * *